(12) United States Patent
Robinson

(10) Patent No.: US 10,213,439 B2
(45) Date of Patent: *Feb. 26, 2019

(54) THERAPEUTIC AND METHOD OF USE

(71) Applicant: Predictive Therapeutics, LLC, Salt Lake City, UT (US)

(72) Inventor: Bradley C. Robinson, North Salt Lake, UT (US)

(73) Assignee: Predictive Therapeutics, LLC, Salt Lake City, UT (US)

( * ) Notice: Subject to any disclaimer, the term of this patent is extended or adjusted under 35 U.S.C. 154(b) by 550 days.

This patent is subject to a terminal disclaimer.

(21) Appl. No.: 14/875,656

(22) Filed: Oct. 5, 2015

(65) Prior Publication Data

US 2016/0022696 A1  Jan. 28, 2016

Related U.S. Application Data

(63) Continuation of application No. 14/281,127, filed on May 19, 2014, now Pat. No. 9,161,941, and a continuation of application No. 14/281,172, filed on May 19, 2014, now Pat. No. 9,149,499.

(60) Provisional application No. 61/825,587, filed on May 21, 2013.

(51) Int. Cl.
| | |
|---|---|
| *A61K 36/00* | (2006.01) |
| *A61K 31/567* | (2006.01) |
| *A61K 31/12* | (2006.01) |
| *A61K 31/192* | (2006.01) |
| *A61K 31/415* | (2006.01) |
| *A61K 31/536* | (2006.01) |
| *A61K 31/5415* | (2006.01) |
| *A61K 45/06* | (2006.01) |
| *A61K 31/138* | (2006.01) |
| *A61K 31/585* | (2006.01) |
| *A61K 31/352* | (2006.01) |
| *A61K 31/57* | (2006.01) |
| *A61K 36/185* | (2006.01) |
| *A61K 38/38* | (2006.01) |

(52) U.S. Cl.
CPC ............ *A61K 31/567* (2013.01); *A61K 31/12* (2013.01); *A61K 31/138* (2013.01); *A61K 31/192* (2013.01); *A61K 31/352* (2013.01); *A61K 31/415* (2013.01); *A61K 31/536* (2013.01); *A61K 31/5415* (2013.01); *A61K 31/57* (2013.01); *A61K 31/585* (2013.01); *A61K 36/00* (2013.01); *A61K 36/185* (2013.01); *A61K 38/385* (2013.01); *A61K 45/06* (2013.01)

(58) Field of Classification Search
CPC ....................................................... A61K 36/00
USPC ....................................................... 424/725
See application file for complete search history.

(56) References Cited

U.S. PATENT DOCUMENTS

| | | | |
|---|---|---|---|
| 8,123,787 B2 | 2/2012 | Ogilvie et al. | |
| 8,641,738 B1 | 2/2014 | Ogilvie et al. | |
| 8,932,993 B1 | 1/2015 | Ward et al. | C12Q 1/6883 |
| 9,149,499 B1 | 10/2015 | Robinson | |
| 9,161,941 B2 | 10/2015 | Robinson | |
| 9,370,431 B2 | 6/2016 | Ogilvie et al. | |
| 9,434,991 B2 | 9/2016 | Ward et al. | |
| 9,623,152 B2 | 4/2017 | Ogilvie et al. | |
| 9,757,152 B2 | 9/2017 | Ogilvie et al. | |
| 2005/0101579 A1 | 5/2005 | Shippen | 514/167 |
| 2006/0246135 A1 | 11/2006 | Nagi et al. | 424/469 |
| 2008/0306034 A1 | 12/2008 | Ward | 514/170 |
| 2009/0170823 A1 | 7/2009 | Diliberti | 514/171 |
| 2017/0112881 A1 | 4/2017 | Robinson | |
| 2018/0008314 A1 | 1/2018 | Ogilvie et al. | |

FOREIGN PATENT DOCUMENTS

| | | |
|---|---|---|
| JP | H04178359 A | 6/1992 |
| JP | 2004537504 A | 12/2004 |
| JP | 2006248904 A | 9/2006 |
| WO | WO-2009075838 A2 | 6/2009 |
| WO | WO-2014189836 A1 | 11/2014 |

OTHER PUBLICATIONS

Amer, et al. "Endometriosis", Obstetrics, Gynaecology & Reproductive Medicine, Elsevier, Amsterdam, NL, vol. 18, No. 5, May 1, 2008 (May 1, 2008), pp. 126-133.
Efstathiou, et al. Nonsteroidal antiinflammatory drugs differentially suppress endometriosis in a murine model. Fertil Steril. Jan. 2005;83(1):171-81.
EP14801452.5 Extended European Search Report dated Nov. 25, 2016.
Hertweck; et al., "Hertweck, et al. Common problems in pediatric and adolescent gynecology. Expert Review of Obstetrics & Gynecology. May 2010; 5(3):311-327.".
Mihalyi; et al., "Mihalyi, et al. Emerging drugs in endometriosis. Expert Opin Emerg Drugs. Sep. 2006;11(3):503-24.".
PCT/US2014/038601 International Search Report and Written Opinion dated Sep. 18, 2014.
Schafer, et al. Conservative therapy of chronic endometriosis (Medikamentöse Therapie der chronischen Endometriose). Gynäkologische Endokrinologie. 2011; 9(4):247-256 (with English abstract).

(Continued)

*Primary Examiner* — Michael V Meller
(74) *Attorney, Agent, or Firm* — Wilson, Sonsini, Goodrich & Rosati, PC

(57) ABSTRACT

The present invention is a compound comprising an anti-inflammatory drug component consisting preferably of at least one of an NSAID portion and a cannabis portion and at least one of a progestin component and a progesterone component. The compound may take for instance the form of a pill or pellet (for oral internal use or for subdermal implantation), an injectable solution, or a suppository. The compound is intended for use in treating subjects having or being at increased risk—especially genetically determined risk—of developing endometriosis. The compound may also be used for treating other disorders or as a contraceptive.

7 Claims, No Drawings

(56) References Cited

OTHER PUBLICATIONS

Schrager, et al. Evaluation and treatment of endometriosis. Am Fam Physician. Jan. 15, 2013;87(2):107-13.
Streuli, et al. An update on the pharmacological management of endometriosis. Expert Opin Pharmacother. Feb. 2013;14(3):291-305.
The American College of Obstetricians and Gynecologists. What is endometriosis? Copyright Oct. 2012. Available at https://www.acog.org/-/media/For-Patients/faq013.pdf. Accessed Apr. 26, 2018.
U.S. Appl. No. 14/281,127 Notice of Allowance dated Sep. 14, 2015.
U.S. Appl. No. 14/281,172 Notice of Allowance dated Aug. 27, 2015.
Rodriguez, GC et al, NSAIDs and progestins synergistically enhance cell death in ovarian epithelial cells, AJOG, Mar. 2012, p. 253e1-253e9.
Ampio Pharmaceuticals, Prospectus Supplement, Ampio Website, 2011, pp. 1-10.
Lilic et al, Genesis, clinical Presentation, Diagnosis and Treatment of Uterine Myomas, ACTA, 2007, pp. 33-40.
Nasser et al, Management of Pelvic Pain from Dysmenorrhea or Endometriosis, JABFP, 2004, pp. S43-S47.
Schweppe, KW, The Current Place of Progestins in the Treatment of Endometriosis, Obstet Gynecol., 2012, pp. 1-11.
Wieser et al, Sulindac Suppresses Nuclear Factor-kB Activation and RANTES Gene and Protein Expression in Endometrial Stroma Cells from Women with Endometriosis, JCEM, 2005, pp. 6441-6447.
Abomaray, Fawaz. Mesenchymal Stem Cells and Endometriosis. Karolinska Institutet, created Feb. 10, 2015, p. 1.
Figueira, et al. Stem Cells in Endometrium and their Role in the Pathogenesis of endometriosis. NIH, Mar. 2011, pp. 1-10.
Ghobadi, et al. Regenerative Potential of Endometrial Stem Cells: A Mini Review. WJPS, Jan. 2015, pp. 3-8.
Goncalves, et al. Mesenchymal Stem Cells Treatment Improves the Endometriosis Proliferation in Cell Culture. FASEB, 2013, p. 1.
Khademi, et al. Human Endometrial Adult Stem Cells can be Differentiated into Hepatocyte Cells. JMHI, 2013, pp. 30-33.
Meng, et al. Endometrial Regenerative Cells: A Novel Stem Cell Population. JTM, Nov. 15, 2005, pp. 1-10.
Tsai, Eing-Mei. Stem Cell as the Novel Pathogenesis of Endometriosis, INTECH, 2012, pp. 263-276.
U.S. Appl. No. 12/341,289 Notice of Allowance dated Nov. 7, 2011.
U.S. Appl. No. 12/341,289 Office Action dated Apr. 12, 2010.
U.S. Appl. No. 12/341,289 Office Action dated Aug. 6, 2010.
U.S. Appl. No. 12/341,289 Office Action dated Dec. 30, 2010.
U.S. Appl. No. 12/341,289 Office Action dated Jul. 24, 2009.
U.S. Appl. No. 12/341,289 Office Action dated Mar. 11, 2009.
U.S. Appl. No. 12/341,289 Office Action dated May 20, 2009.
U.S. Appl. No. 12/341,289 Office Action dated Nov. 17, 2009.
U.S. Appl. No. 13/357,800 Office Action dated Sep. 17, 2013.
U.S. Appl. No. 14/170,691 Office Action dated Feb. 4, 2015.
U.S. Appl. No. 14/170,691 Office Action dated Jan. 22, 2015.
U.S. Appl. No. 15/186,914 Notice of Allowance dated Dec. 15, 2016.
U.S. Appl. No. 15/186,914 Office Action dated Sep. 8, 2016.
U.S. Appl. No. 15/488,870 Notice of Allowance dated Aug. 3, 2017.

THERAPEUTIC AND METHOD OF USE

CROSS REFERENCE TO RELATED APPLICATIONS

This nonprovisional utility patent application is a continuation of and claims the benefit under 35 USC § 120 to co-pending U.S. application Ser. No. 14/281,127 filed May 19, 2014 and since issued as U.S. Pat. No. 9,161,941 on Oct. 20, 2015, which claims the benefit under 35 USC § 119(e) of US provisional application No. 61/825,587 filed May 21, 2013, and is a continuation of and claims the benefit under 35 USC § 120 to U.S. application Ser. No. 14/281,172 filed May 19, 2014 and since issued as U.S. Pat. No. 9,149,499 on Oct. 6, 2015, which claims the benefit under 35 USC § 119(e) of US provisional application No. 61/825,587 filed May 21, 2013, all of which are expressly incorporated herein in their entirety by this reference.

FIELD OF THE INVENTION

The present invention relates to therapeutics, and more especially NSAID and/or cannabis based therapeutics for use in treating those known to have or be at increased risk of endometriosis and other ailments.

BACKGROUND OF THE INVENTION

Endometriosis is a common gynecological disorder. Many therapeutics including progestins and uses of such therapeutics in the treatment of endometriosis are well known. Examples of such therapeutics and methods are taught in US patent application 20080306034 to Ward and in U.S. patent application Ser. No. 13/788,913 to Ward et al. which are incorporated herein in their entirety by this reference. Further, it has been shown that the concurrent administration of both an NSAID (Nonsteroidal Anti-Inflammatory Drug) and a progestin can provide an increased synergistic effect in the treatment of a disorder as compared to what might be obtained by the administration of an NSAID and/or a progestin separately. Moreover, such concurrent administration may allow for reduced dosages of an NSAID and/or a progestin as compared to a required dosage of an NSAID and a progestin administered separately. An example of such concurrent administration is taught in "Rodriguez, G C et al, NSAIDs and progestins synergistically enhance cell death in ovarian epithelial cells, AJOG, March 2012, pg 253e1-253e9" which is incorporated herein in its entirety by this reference. It is further known that cannabis has been shown to reduce pain and/or inflammation and/or reduce sensitivity to pain and may have fewer or none of the side effects of other NSAIDs (see Appxs A and B).

SUMMARY OF THE INVENTION

The present invention is a compound comprising an anti-inflammatory drug component and at least one of a progestin portion and a progesterone portion. The anti-inflammatory drug component preferably includes at least one of an NSAID component and a cannabis portion. The compound may optionally also include both an NSAID portion in addition to and separate from the cannabis based portion. For the purposes of this invention, where reference is used to an NSAID, unless indicated otherwise, such NSAID shall be understood to be a separate and distinct component from a cannabis component. The compound may take for instance the form of a pill or pellet (for oral internal use or for subdermal implantation), an injectable solution, or a suppository. The compound is intended for use in treating subjects having or being at increased risk—especially genetically determined risk—of developing endometriosis. The compound may also be used for treating other disorders such as chronic pain, and more especially chronic pelvic pain or as a contraceptive.

DETAILED DESCRIPTION OF THE INVENTION

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are included to provide a thorough understanding of embodiments of the invention. One skilled in the relevant art will recognize, however, that the invention can be practiced without one or more of the specific details, or with other methods, components, materials, and so forth. In other instances, well-known structures, materials, or operations are not shown or described in detail to avoid obscuring aspects of the invention.

A first embodiment of the invention is a therapeutic compound for use in treating endometriosis and like disorders and preferably in pill form comprising a compound including at least one of an NSAID component and a cannabis component and at least one of a progestin component and a progesterone component. In practice, a subject being determined to have endometriosis or at increased risk of developing endometriosis, and more especially being determined to be genetically predisposed to increased risk of developing endometriosis, is orally administered a therapeutically effective amount of the compound so as to alleviate, cure, or prevent the symptoms of endometriosis. The therapeutic compound may be likewise administered for use as a contraceptive.

A second embodiment of the invention is a therapeutic compound for use in treating endometriosis and like disorders and preferably in pellet form comprising a compound including at least one of an NSAID component and a cannabis component and at least one of a progestin component and a progesterone component. In practice, a subject being determined to have endometriosis or at increased risk of developing endometriosis, and more especially being determined to be genetically predisposed to increased risk of developing endometriosis, is administered a therapeutically effective amount of the compound by implanting the compound subdermally into the subject so as to alleviate, cure, or prevent the symptoms of endometriosis. The therapeutic compound may be likewise administered for use as a contraceptive.

A third embodiment of the invention is a therapeutic compound for use in treating endometriosis and like disorders and preferably in solution form comprising a compound including at least one of an NSAID component and a cannabis component and at least one of a progestin component and a progesterone component. In practice, a subject being determined to have endometriosis or at increased risk of developing endometriosis, and more especially being determined to be genetically predisposed to increased risk of developing endometriosis, is administered a therapeutically effective amount of the compound by injecting the compound subdermally into the subject so as to alleviate, cure, or prevent the symptoms of endometriosis. The therapeutic compound may be likewise administered for use as a contraceptive.

A fourth embodiment of the invention is a therapeutic compound for use in treating endometriosis and like disorders and preferably in suppository form comprising a compound including at least one of an NSAID component and a cannabis component and at least one of a progestin component and a progesterone component. In practice, a subject being determined to have endometriosis or at increased risk of developing endometriosis, and more especially being determined to be genetically predisposed to increased risk of developing endometriosis, is administered a therapeutically effective amount of the compound by placing the compound into a body orifice of the subject (e.g. vaginally or rectally) so as to alleviate, cure, or prevent the symptoms of endometriosis. The therapeutic compound may be likewise administered for use as a contraceptive.

It shall be noted that the progestin disclosed herein may include any of a first generation progestin (estrane) including norethindrone, norethynodrel, norethindrone acetate, and ethynodiol diacetate, a second generation progestin (gonane) including levonorgestrel, norethisterone, and norgestrel, a third generation progestin (gonane) including desogestrel, gestodene, norgestimate, drospirenone, and a fourth generation progestin including dienogest, nestorone, nomegestrol acetate, and trimegestone. It shall also be noted that the progesterone disclosed herein may include tanaproget. It shall also be noted that the cannabis component is preferably free of a THC portion. It shall also be noted that the cannabis component may include any of a nabilone, dronabinol, and nabiximols. It shall also be noted that the NSAID disclosed herein may include any of a salicylate including aspirin (acetylsalicylic acid), diflunisal, and salsalate, a propionic acid derivative including ibuprofen, dexibuprofen, naproxen, fenoprofen, ketoprofen, dexketoprofen, flurbiprofen, oxaprozin, and loxoprofen, an acetic acid derivative including indomethacin, tolmetin, sulindac, etodolac, ketorolac, diclofenac, and nabumetone, an enolic acid (oxicam) derivative including piroxicam, meloxicam, tenoxicam, droxicam, lornoxicam, and isoxicam, a fenamic acid derivative (fenamates) including efenamic acid, meclofenamic acid, flufenamic acid, and tolfenamic acid, a selective COX-2 inhibitor (Coxibs) including celecoxib, rofecoxib, valdecoxib, parecoxib, lumiracoxib, etoricoxib, and firocoxib (used in dogs and horses), a sulphonanilide including nimesulide, an other NSAID including licofelone (acts by inhibiting LOX (lipooxygenase) & COX and hence known as LOX/COX inhibitor) and lysine clonixinate, and a natural NSAID including hyperforin, figwort, and calcitriol (vitamin D). It shall also be noted that the compound disclosed herein may include a biologic component including AMPION. It shall also be noted that the therapeutic compound disclosed herein is also useful in increasing dosage accuracy and administration convenience as compared to concurrent administration of separate NSAID and progestin and/or progesterone components.

An exemplary therapeutic compound conforming with any of the disclosed embodiments may comprise for instance a compound including at least one of nabilone, dronabinol, and nabiximols, and at least one of a progestin component and a progesterone component and optionally at least one of naproxen, meloxicam, and celecoxi. A further exemplary therapeutic compound conforming with any of the disclosed embodiments may comprise for instance a compound including at least one of nabilone, dronabinol, and nabiximols and at least one of a progestin component and a progesterone component and optionally at least one of piroxicam, sulindac, and nabumetone. Still further an exemplary therapeutic compound conforming with any of the disclosed embodiments may comprise for instance a compound including 200 to 400 mg (milligrams) of nabilone and 250 to 450 µg (micrograms) of norethindrone preferably administered as a once daily dosage. Still further an exemplary therapeutic compound conforming with any of the disclosed embodiments may comprise for instance a compound including 200 to 400 mg (milligrams) of nabilone and 250 to 450 µg (micrograms) of norethindrone preferably administered as a once daily dosage. Still further an exemplary therapeutic compound conforming with any of the disclosed embodiments may comprise for instance a compound including approximately 300 mg of nabilone and approximately 350 µg of norethindrone preferably administered as a once daily dosage.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A pill or pellet consisting essentially of cannabis, human serum albumin, a compound selected from the group consisting of ibuprofen, naproxen, and a combination thereof, and a compound selected from the group consisting of progestin, progesterone, and a combination thereof.

2. The pill or pellet of claim 1 consisting essentially of the ibuprofen, the cannabis, the human serum albumin, and the compound selected from the group consisting of the progestin, the progesterone, and the combination thereof.

3. The pill or pellet of claim 1 consisting essentially of the naproxen, the cannabis, the human serum albumin, and the compound selected from the group consisting of the progestin, the progesterone, and the combination thereof.

4. The pill or pellet of claim 1 consisting essentially of the ibuprofen and the naproxen, the cannabis, the human serum albumin, and the compound selected from the group consisting of the progestin, the progesterone, and the combination thereof.

5. The pill or pellet of claim 1 consisting essentially of the progestin, the cannabis, the human serum albumin, and the compound selected from the group consisting of the ibuprofen, the naproxen, and the combination thereof.

6. The pill or pellet of claim 1 consisting essentially of the progesterone, the cannabis, the human serum albumin, and the compound selected from the group consisting of the ibuprofen, the naproxen, and the combination thereof.

7. The pill or pellet of claim 1 consisting essentially of the progestin and the progesterone, the cannabis, the human serum albumin, and the compound selected from the group consisting of the ibuprofen, the naproxen, and the combination thereof.

* * * * *